United States Patent
Wada et al.

(10) Patent No.: US 7,214,521 B2
(45) Date of Patent: May 8, 2007

(54) INULIN SYNTHASE AND PROCESS FOR PRODUCING INULIN BY USING THE SAME

(75) Inventors: Tadashi Wada, Shizuoka (JP); Masao Ohguchi, Shizuoka (JP)

(73) Assignee: Fuji Nihon Seito Corporation, Tokyo (JP)

(*) Notice: Subject to any disclaimer, the term of this patent is extended or adjusted under 35 U.S.C. 154(b) by 256 days.

(21) Appl. No.: 10/311,318

(22) PCT Filed: Feb. 16, 2001

(86) PCT No.: PCT/JP01/01133

§ 371 (c)(1),
(2), (4) Date: Dec. 30, 2002

(87) PCT Pub. No.: WO02/00865

PCT Pub. Date: Jan. 3, 2002

(65) Prior Publication Data

US 2003/0190711 A1    Oct. 9, 2003

(30) Foreign Application Priority Data

Jun. 28, 2000    (JP)    ............... 2000-195245

(51) Int. Cl.
C12N 9/12 (2006.01)
C12N 1/20 (2006.01)
C12N 9/00 (2006.01)
C07H 21/04 (2006.01)

(52) U.S. Cl. .............. 435/194; 435/4; 435/6; 435/69.1; 435/183; 435/252.3; 435/252.5; 435/320.1; 536/23.2; 536/23.5; 536/23.6; 536/23.7

(58) Field of Classification Search .............. 435/4, 435/6, 69.1, 183, 193, 252.3, 320.1; 536/23.2, 536/23.7; 530/350
See application file for complete search history.

(56) References Cited

U.S. PATENT DOCUMENTS

| 5,952,205 A | 9/1999 | Catani et al. |
| 6,242,225 B1 | 6/2001 | Catani et al. |
| 6,423,833 B1 | 7/2002 | Catani et al. |

FOREIGN PATENT DOCUMENTS

WO    WO 00/31287    6/2000

OTHER PUBLICATIONS

Koops et al. (Plant Physiol., 1996, vol. 110(4):1167-1175).*
T. Wada, et al., Bioscience, Biotechnology, and Biochemistry, vol. 67, No. 6, XP-002277857, pp. 1327-1334, "A Novel Enzyme of *Bacillus* sp. 217C-11 That Produces Inulin from Sucrose", Jun. 2003.

(Continued)

*Primary Examiner*—Manjunath Rao
(74) *Attorney, Agent, or Firm*—Oblon, Spivak, McClelland, Maier & Neustadt, P.C.

(57) ABSTRACT

The present invention relates to a novel inulin synthase having a function and a substrate specificity of acting on sucrose to produce inulin, but not acting on kestose, maltose, lactose, trehalose and cellobiose; and a process for producing inulin comprising the step of allowing the synthase, a culture fluid or cultured cells of a microorganism producing the synthase, or a treated product thereof to contact with sucrose to produce inulin.

4 Claims, 5 Drawing Sheets

EFFECT OF TEMPERATURE ON ENZYME ACTIVITY OF THE INULIN SYNTHASE OF THE PRESENT INVENTION

OTHER PUBLICATIONS

S.A.F.T. Van Hijum, et al., Applied and Environmental Microbiology, vol. 65, XP-002264246, pp. 73-96, "Molecular Characterization of a Novel Fructosyltransferase From *Lactobacillus reuteri* Synthesizing a High Molecular Weight Fructan with β-(2→ 1) Linked Fructosyl Units in *Escherichia coli*", 1999.

B.W. Kim et al.: "Selective production of GF4-fructooligosaccharide from sucrose by a new transfructosylating enzyme" Biotechnol. Lett., vol. 20, No. 11, pp. 1031-1034.

E.M. Hellwage et al.: "Difference in chain length distribution of inulin from *Cynara scolymus* and *Helianthus tuberosus* are reflected in a transient plant expression system using the respective 1-FFT cDNAs" FEBS Lett., vol. 427, pp. 25-28 1998.

* cited by examiner

SEQUENCE LISTING

<160> NUMBER OF SEQ ID NOS: 1

<210> SEQ ID NO 1
<211> LENGTH: 30
<212> TYPE: PRT
<213> ORGANISM: Bacillus sp.217C-11

<400> SEQUENCE: 1

```
Glu Glu Ile Asn Ser Asp Tyr Thr Ser Ile Trp Ser Arg Gln Gln Ala
1               5                   10                  15

Glu Lys Val Thr Pro Thr Asp Lys Thr Thr Ala Pro Lys Ile
            20                  25                  30
```

INULIN SYNTHASE AND PROCESS FOR PRODUCING INULIN BY USING THE SAME

FIELD OF THE INVENTION

The present invention relates to a novel inulin synthase and a process for producing inulin using the inulin synthase.

BACKGROUND ART

Inulin is a type of polysaccharides, and is widely distributed throughout the natural world. Colloidal inulin exists in the tubers of plants of the family Asteraceae, such as dahlia, Jerusalem artichoke and *Inula japonica* or in the root of chicory. Unlike starch, inulin is dissolved in warm water, and has a structure wherein D-fructofuranose is polymerized by dehydration onto the fructose side of sucrose by $\beta$-(2→1) linkages. The molecular weight differs depending on the chain length of fructose. Plant-derived inulin can be said to be an aggregate of compounds differing in their molecular weights. The average degree of polymerization ranges from 32 to 34 according to Dictionary of Biological Science (IWANAMI SHOTEN, PUBLISHERS, 2nd edition (1978)), and is about 30 according to Dictionary of Physics and Chemistry (IWANAMI SHOTEN, PUBLISHERS, 3rd edition (1979)). The molecular weight is about 5,000 according to Dictionary of Biochemistry (TOKYO KAGAKU DOZIN CO., LTD., 1st edition (1985)), while according to the literature of W. Praznik (Journal of Chromatography, 348, 187–197 (1985)) the mean molecular weight is 2,282 to 17,000 while the degree of polymerization somewhat varies depending on the types of plants. The molecular size of inulin is limited within a certain range.

Since inulin is dietary fiber that is difficult to digest, it has attracted interest as a dietary fiber. Further, as its effects include, for example, increasing the growth of *Bifidobacterium*, the demand for inulin is increasing amidst the recent boom in health-consciousness.

Inulin has been mainly produced in areas outside Japan where inulin is produced by cultivating a plant, such as dahlia, chicory, or Jerusalem artichoke, and drying the extracts from the rhizoma, and it is generally consumed as a foodstuff. Inulin is not produced in Japan because commercial cultivation of these plants is difficult.

To acquire inulin in Japan, there is thus no choice but to import. Such imported inulin is more expensive than a domestic substance having functions analogous to inulin. This can be considered as a problem related with industrial use. In addition, the yield of plant-derived inulin depends on the crop conditions, as the raw material of inulin is extracted from the plant. Besides, a problem associated with plant-derived inulin is that the inulin content reduces in value by, for example, autolysis, unless extraction is performed immediately after harvest. Furthermore, in the case of plant-derived inulin, purification is extremely difficult because of varied fructose chain lengths. Thus, currently available plant-derived inulin is commercialized by roughly fractionating as a raw material a solution containing inulin with varied chain lengths, and then drying by spraying. Therefore, there remains a problem that even though the purity as inulin may be high, there is a lack of uniformity in the chain lengths.

On the other hand, the above-mentioned higher plants from which inulin can be extracted obviously contain an enzyme for producing inulin, and it has already been shown by M. Luscher et al. (FEBS Letter 385, 39 (1996)) that inulin is produced from sucrose using an enzyme that is extracted from such a plant. This mechanism is driven by the cooperative action of two types of enzymes: sucrose 1-fructosyltransferase (SST), a sucrose which performs transfer of fructosyl between sucroses, and $\beta$-(2→1) fructan 1-fructosyltransferase (FFT), a $\beta$-(2→1) fructan which transfers fructose moieties between fructans having a degree of polymerization of 3 or more.

However, it is impractical to employ this mechanism on an industrial scale to prepare a large amount of enzyme from plant bodies, because it is both time- and labor-consuming.

In addition to the plant-derived inulin, a method for producing analogues of inulin by action of microbial enzyme has been reported.

For example, N. Kopeloff et al. reported in 1920 that the conidiospores of *Aspergillus sydowi* have invertase activity and produce a levan type of fructan from sucrose (J. Biol. Chem., 43, 171 (1920)). Later, J. R. Loewenberg et al. revealed that the polysaccharide has an inulin type conformation having $\beta$-(2→1) linkages of fructose (Can. J. Microbiol., 3, 643, (1957)).

Thereafter, G. Kawai et al. reported in 1973 that when conidiospores of *Aspergillus sydowi* were allowed to react with sucrose, production of polyfructan and oligofructan was observed, and that like higher plant-derived inulin, the polyfructan is in the shape of a straight chain having $\beta$-(2→1) linkages, but lacks glucose at its end, and its molecular size is about 20,000,000 which is far greater than that of higher plant-derived inulin (Agric. Biol. Chem., 37, (9), 2111, (1973)).

Then, Nakakuki et al. proposed a method for producing oligofructan and macromolecular fructan by treating sucrose with the cells of *Aspergillus sydowi*. The produced fructan is a linear polyfructan having glucose at its end and having fructose linked by $\beta$-(2→1) linkages. The oligofructan in this case was described as having a degree of polymerization of 5 or less, while the macromolecular fructan has a molecular weight ranging from $1.8 \times 10^5$ to $1.4 \times 10^7$ (JP Patent Publication (Unexamined Application) No. 61-187797).

Harada et al. have also proposed a method for producing polyfructan from sucrose using the conidiospores of *Aspergillus sydowi*, and describe that the molecular weight of the polyfructan in this case was around 10,000,000 (JP Patent Publication (Unexamined Application) No. 5-308885).

Hidaka et al. have proposed a method for producing linear fructan having $\beta$-(2→1) linkages by allowing fructosyltransferase produced by microorganisms belonging to the genus Aspergillus or Fusarium to act on sucrose (JP Patent Publication (Unexamined Application) No. 55-40193). However, the fructan produced in this case is an oligosaccharide wherein 1 to 4 molecules of fructose are bound to sucrose, so that it is defined as a substance different from inulin in molecular size.

Furthermore, Rosell et al. have reported that some of *Streptococcus mutans*, which is considered a pathogen of dental caries, produce enzyme for producing the analogue of inulin (Acta. Chem. Scand., B28, 589). However, the inulin analogue differs from inulin in that it is a quite giant molecule having the molecular weight of 20,000,000, and has $\beta$-(2→6) linkages in a straight chain of $\beta$-(2→1) linkages.

As described above, substances that have been so far produced using enzymes derived from microorganisms are referred to as inulin type polyfructan in order to distinguish them from the plant-derived inulin, because the substances have properties largely differing from those of the above described plant-derived inulin (for example, their molecular size is large or they have a different binding format compared to the plant-derived inulin).

Therefore, there has been no established technology to date for producing inulin using enzyme derived from a microorganism.

SUMMARY OF THE INVENTION

An object of the present invention is to provide a means for efficiently producing inulin of a uniform quality with high purity in large quantities.

As a result of thorough studies to solve the above problems, we have completed the present invention by finding that a microorganism, in particular, a microorganism belonging to the genus *Bacillus,* has enzyme which can solve the above problems.

(i) Specifically, the present invention is an inulin synthase having the following function and substrate specificity: function and substrate specificity: acting on sucrose to produce inulin, but not acting on kestose, maltose, lactose, trehalose and cellobiose.

(ii) Further, the present invention is the inulin synthase of (i) above, wherein said inulin synthase may be obtained from a culture fluid or cultured cells of a microorganism, or a treated product thereof.

(iii) Furthermore, the present invention is the inulin synthase of (ii) above, wherein said microorganism belongs to the genus *Bacillus.*

(iv) Further, the present invention is the inulin synthase of (iii) above, wherein said microorganism belonging to the genus *Bacillus* is *Bacillus* sp. 217C-11 strain (FERM BP-7450).

(v) Furthermore, the present invention is the inulin synthase of any one of (i) to (iv) above, wherein an N-terminal amino acid sequence of said inulin synthase is the sequence shown by SEQ ID NO: 1.

(vi) Further, the present invention is a process for producing inulin, which comprises the step of allowing said inulin synthase of any one of (i) to (v) above, a culture fluid or cultured cells of a microorganism producing said synthase, or a treated product thereof to contact with sucrose to produce inulin.

(vii) Furthermore, the present invention is the process for producing inulin of (vi) above, wherein said microorganism belongs to the genus *Bacillus.*

(viii) Further, the present invention is the process for producing inulin of (vii) above, wherein said microorganism belonging to the genus *Bacillus* is *Bacillus* sp. 217C-11 strain (FERM BP-7450).

This specification includes part or all of the contents as disclosed in the specification and/or drawings of Japanese Patent Application No.2000-195245, which is a priority document of the present application.

BEST MODE TO CARRY OUT THE INVENTION

The process of the present invention is hereafter described in detail.

The inulin synthase (the inulin synthase of (i) above) of the present invention has the function and the substrate specificity of acting on sucrose to produce inulin, but not acting on kestose, maltose, lactose, trehalose and cellobiose.

The above function and the substrate specificity have been determined as described in the later-described Example 1.

As described above, the plant-derived enzyme is known to produce inulin from sucrose by the cooperative action of two types of enzymes. Specifically, inulin is produced from sucrose by a two-step action: in the first step, an enzyme functions to produce 1 molecule of kestose (trissaccharide) from two molecules of sucrose, and in the second step, an enzyme functions to further polymerize the two.

In contrast, the inulin synthase of the present invention has a mechanism for acting on sucrose that is essentially different from that of the existing plant-derived enzyme, because it significantly lacks the liberation of kestose from sucrose and no production of inulin is observed when the enzyme of the present invention is allowed to act on kestose as described above. Therefore, the enzyme of the present invention has never been known and is a novel enzyme for directly synthesizing inulin from sucrose.

The inulin synthase of the present invention has the following physicochemical properties:

Molecular weight: 45,000–50,000

Optimal temperature: 40 to 50° C.

Thermostability: Gradually starts to inactivate as temperature exceeds 45° C. Shows remaining activity of 70% at 50° C., and 40% at 60° C.

Optimal pH: 7 to 8 (45° C.)

pH stability: stable at pH 6 or more.

Each of the above properties was determined by techniques as described below.

Molecular weight: The molecular weight of the inulin synthase of the present invention was measured by a gel filtration method of first protein liquid chromatography (FPLC) using Sephacryl S-300 column and using the purified enzyme sample prepared in Example 1 (described below) of the specification, and using as a marker protein a standard protein manufactured by Bio-Rad (Thyroglobulin (bovine), molecular weight of 670,000; Gammer globulin (bovine), molecular weight of 158,000; Ovalbumin (chicken), molecular weight of 44,000; and Myoglobin (horse), molecular weight of 17,000)).

Optimal Temperature:

A purified enzyme sample (the same as above) is used. The enzyme was allowed to react with a sucrose solution at each temperature (37, 45, 50, 60 and 70° C., and pH 7).

Figure 1:
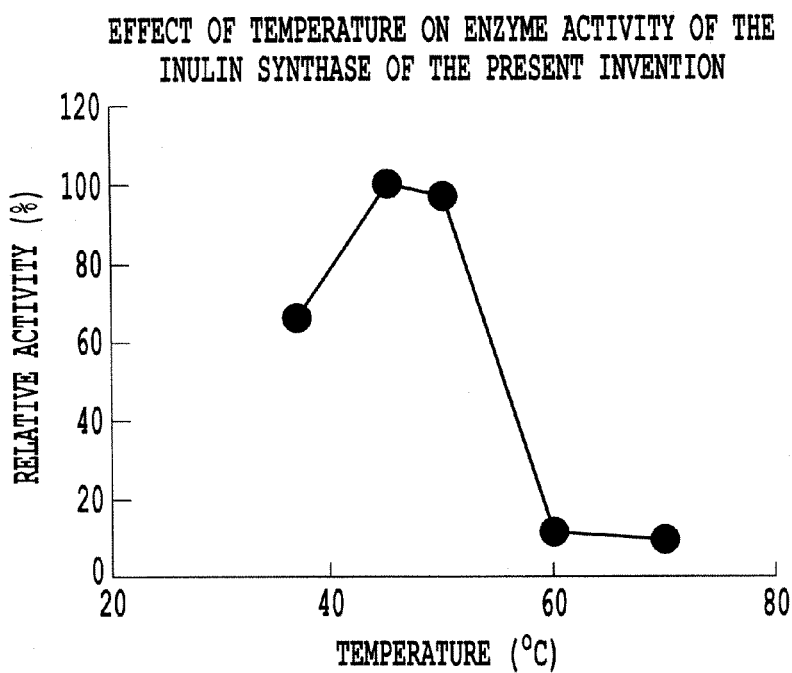
FIG. 1 shows the effect of temperature on the enzyme activity of the inulin synthase of the present invention.

Glucose produced in the reaction solution was quantitatively determined by a glucose oxidase method, and then the activity was obtained from the amount of glucose produced per unit time (FIG. 1 shows the data). As shown in FIG. 1, inactivation of the enzyme was minimized under the above conditions, and the enzyme reaction smoothly proceeded at 45° C. In the above glucose oxidase method, 1 unit of enzyme activity means an amount of enzyme necessary for producing 1 µmole of glucose per minute.

Figure 3:
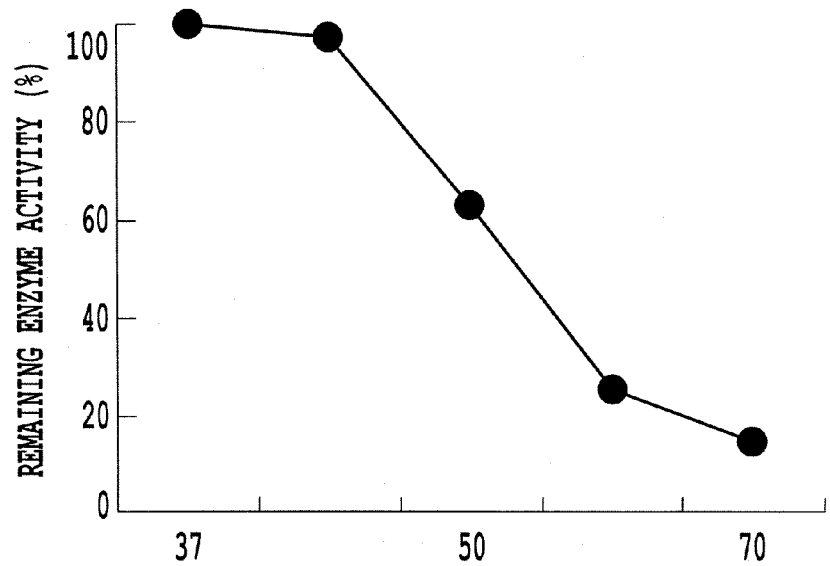
FIG. 3 shows the effect of temperature on the stability of the inulin synthase of the present invention.

Thermostability: The purified enzyme sample (the same as above) which was treated by heat at each temperature (37, 45, 50, 60 and 70° C., and pH 7) for 30 min was allowed to react with a sucrose solution. Glucose produced in the reaction solution was quantitatively determined by the glucose oxidase method. The activity was obtained from the amount of glucose produced per unit hour (FIG. 3 shows the data).

Figure 2:
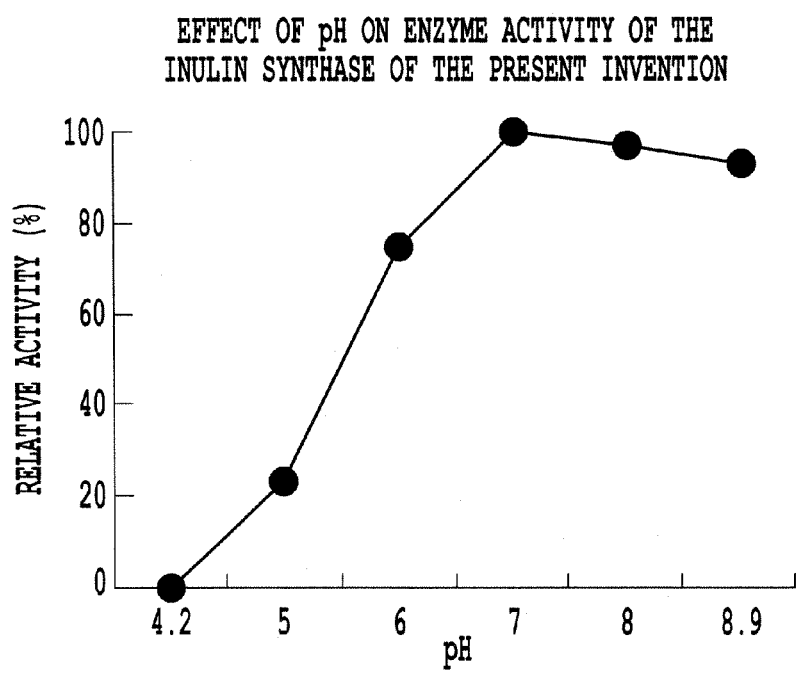
FIG. 2 shows the effect of pH on the enzyme activity of the inulin synthase of the present invention.
Figure 4:
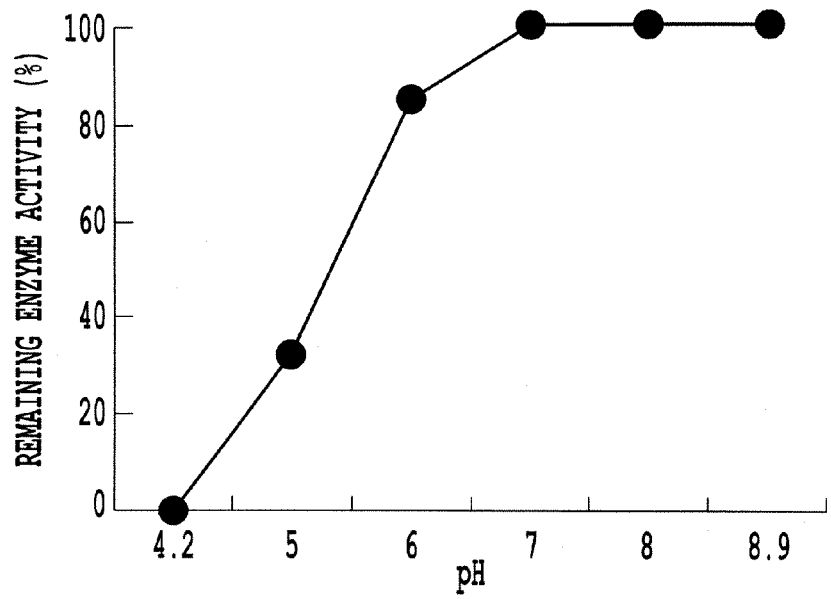
FIG. 4 shows the effect of pH on the stability of the inulin synthase of the present invention.

Optimum pH: The purified enzyme sample (the same as above) was allowed to react at 37° C. with a sucrose solution at each pH (4.2, 5.0, 6.0, 7.0, 8.0 and 8.9). Glucose produced in the reaction solution was quantitatively determined by the glucose oxidase method. The activity was obtained from the amount of glucose produced per unit hour (FIG. 2 shows the data).

pH stability: The purified enzyme sample (the same as above) was prepared respectively at each pH (4.2, 5.0, 6.0, 7.0, 8.0 and 8.9), allowed to stand at 4° C. for 24 hours, and then allowed to react with a sucrose solution at 37° C. Glucose produced in the reaction solution was quantitatively determined by the glucose oxidase method. The activity was obtained from the amount of glucose produced per unit time (FIG. 4 shows the data).

Furthermore, when the amino acid sequence of the inulin synthase of the present invention was analyzed as described in the later-described Example 1, it was found to have a partial amino acid sequence: Glu-Glu-Ile-Asn-Ser-Asp-Tyr-Thr-Ser-Ile-Trp-Ser-Arg-Gln-Gln-Ala-Glu-Lys-Val-Thr-Pro-Thr-Asp-Lys-Thr-Thr-Ala-Pro-Lys-Ile (SEQ ID NO: 1) at the N-terminus.

Therefore, for example, the inulin synthase of the present invention can be obtained by determining the nucleotide sequence encoding the above partial amino acid sequence, designing and synthesizing appropriate primers based on the nucleotide sequence, and then performing PCR. Once the entire nucleotide sequence encoding the inulin synthase of the present invention is determined, for example, the inulin synthase of the present invention can be obtained by cloning the entire gene sequence, and allowing the cloned sequence to express by known genetic engineering techniques. Alternatively, the inulin synthase of the present invention described in (ii) above can also be collected from the culture fluid or the cultured cells of a microorganism which produces the enzyme, or the treated product thereof.

Examples of the above microorganism are not specifically limited, so far as they produce the inulin synthase of the present invention, and include known strains, or new strains isolated from soil, seawater or the like. Alternatively, a mutant strain prepared by treatment for mutation (for example, ultraviolet irradiation, nitrosoguanidine (NTG) and ethyl methanesulfonate (EMS)) to have an enzyme with improved ability to produce inulin may be used.

Specifically, the above microorganism may be, for example, a microorganism belonging to the genus *Bacillus* (inulin synthase of the above (iii)), particularly *Bacillus* sp. 217C-11 strain (FERM BP-7450) which was internationally deposited on Jun. 14, 2000 under The Budapest Treaty at the International Patent Organism Depositary, National Institute of Bioscience and Human-Techonology, National Institute of Advanced Industrial Science and Technology in the Ministry of Economy, Trade and Industry (Tsukuba Central 6, 1-1-1, Higashi, Tsukuba-shi, Ibaraki, Japan) (the former Fermentation Research Institute, Agency of Industrial Science and Technology in the Ministry of International Trade and Industry, 1-1-3, Higashi, Tsukuba-shi, Ibaraki, Japan) (inulin synthase of the above (iv)).

We have isolated the *Bacillus* sp. 217C-l 1 strain (FERM BP-7450) for the first time from nature. As a result of examination based on the following mycological properties according to Bergey's Manual of Systematic Bacteriology (Vol. 2 (1986)), this strain has been determined as a strain belonging to the genus *Bacillus*.

Mycological Property of *Bacillus* sp. 217C-11 Strain (FERM BP-7450)

(a) Morphology
1) Cell shape and size: Bacillus, 1×2 to 3 µm
2) Mobility: motile
3) Spore: spore-forming Bacilli
4) Gram stain: uncertain (b) Growth State in Media
1) Colony morphology: round, wavelike periphery, low convexity, gloss and cream (c) Physiological Property
1) catalase: positive
2) oxidase: positive
3) hydrolysis of gelatine: negative
4) Growth temperature: 25 to 37° C. No growth at 50° C. or more
5) Behavior toward oxygen: aerobe (capable of growing under anaerobic conditions)
6) Production of acid from a saccharide (+: acid production, −: no acid production)
   Fructose +
   Glucose +
   Xylose −
   Sucrose +
   Lactose +
   Maltose +
   Trehalose +
   Mannose +
   Melibiose +
   Inulin +
   Cellobiose +
   Mannitol −
   Glycerol −
7) Reduction of nitrate: no reduction
8) β-galactosidase: positive
9) Arginine dihydrolase: negative
10) Lysine decarboxylase: negative
11) Ornithine decarboxylase: negative
12) Capability of using citric acid: negative
13) Production of hydrogen sulfide: negative
14) Urease: negative
15) Triptophan deaminase: negative
16) Indole production: negative
17) Acetoin production: negative
18) Gelatinase: negative
19) Hydrolysis of casein: negative
20) Hydrolysis of hippurate: negative
21) Hydrolysis of starch: positive The term "cultured cells" means the above microorganism that is cultured under appropriate conditions, and may be viable cells or freeze-dried cells, or may be in the form of acetone powder or the like.

Examples of the treated product of the cultured cells are not specifically limited, so far as the enzyme of the present invention can be collected from the product without losing the function of the enzyme. For example, the treated product means disrupted cells, cell extracts (liquid), immobilized cells and the like of the above cultured cells.

The disrupted cells and the cell extracts (liquid) of the cultured cells mean substances, extracts and the like, which are obtained by disrupting the cells by a known disruption method, such as ultrasonic breaking, DynoMill disruption and French press disruption. The term "immobilized cells" means the above cells which are immobilized by a known immobilization method, such as an entrapment method or a carrier-binding method, and then subjected to cross-linking if necessary. Examples of the entrapment method include a method using natural polymers, such as carrageenan or alginic acid.

The inulin synthase of the present invention can be collected from the culture fluid of a microorganism, for example, as described below.

Culturing of Microorganism

First, the above microorganism is cultured under appropriate conditions.

An appropriate medium for culturing the above microorganism contains a carbon source, nitrogen source, minerals and the like, but the nutrient sources are not limited thereto. If necessary, nutrient sources normally used for culturing, such as amino acids and vitamin can also be used appropriately.

Examples of the carbon source that may be added to the medium include known carbon sources in the art, such as a sugar, for example, sucrose, glucose, fructose and maltose. However, the most preferable medium for culturing *Bacillus* sp. 217C-11 strain (FERM BP-7450) as a microorganism is a liquid medium containing sucrose as a main carbon source, which can improve the activity of the inulin synthase of the present invention. These carbon sources may be used at an appropriate concentration (for example, 0.5 to 5.0%), either independently or by mixing. In addition, these carbon sources may be in an isolated or purified form, or may be contained in other substances. For example, when sucrose is used as a carbon source, a sucrose inclusion, such as sucrose brown sugar or molasses, may be used instead of purified sucrose.

Examples of a nitrogen source that is added to the medium include, but are not limited to, an organic nitrogen source, such as peptone, meat extract, yeast extract and corn steep liquor, and an inorganic nitrogen source, such as ammonium salt of sulfuric acid, nitric acid and phosphoric acid. The nitrogen source may be used independently or a mixture of the nitrogen sources may be used.

Examples of an inorganic salt that can be used independently or used in combination include, but are not limited to, sulfate, hydrochloride, carbonate, nitrate, phosphate and the like of potassium, sodium, calcium, magnesium, manganese, iron and the like.

The pH of a medium having the above composition ranges from pH 6 to 9, and preferably pH 7 to 8. A culturing temperature preferably ranges from 25° C. to 37° C.

The above microorganism may be shake-cultured or cultured under aeration condition using a jar fermentor. A culturing time may be a time period during which a microorganism can grow or longer, and is 5 to 96 hours, and preferably, 15 to 72 hours.

Collection of Inulin Synthase of the Present Invention

Collection of the inulin synthase of the present invention can be performed, for example, by collecting the culture fluid, since the enzyme activity of the inulin is mainly found in the culture supernatant of the above microorganism (cultured cell).

The culture fluid can be collected by a known solid-liquid separation method, such as a method for centrifuging a culture fluid, or a method for separating a culture fluid by membrane filtration, or the like. However, the method is not limited thereto.

The inulin synthase of the present invention collected as described above can be used intact (in a liquid form, such as the above culture fluid) in the later-described process for producing the inulin of the present invention as a crude enzyme solution, but is preferably used in a concentrated form.

Examples of a concentration method that is used herein include, but are not limited to, techniques known to a person skilled in the art, such as solvent sedimentation using acetone or isopropanol, ammonium sulfate fractionation and membrane concentration.

Furthermore, the above enzyme solution may be immobilized by a known method. Examples of an immobilization method that is used herein include, but are not limited to, a method of binding to an ion exchanger, a method of covalent binding and adsorption with resin, membrane or the like, and an entrapment method using high molecular substances.

The inulin synthase of the present invention can be used intact as a crude enzyme (for example, the above crude enzyme solution), or may be further purified by a method known by a person skilled in the art, such as ion exchange chromatography using a commercially available resin and gel filtration chromatography.

Examples of the above resin that can be used herein include TSKgel DEAE TOYOPEARL 650 and TOYOPEARL HW55 manufactured by TOSOH CORPORATION, and Sephacryl S-300 manufactured by Pharmacia.

Specifically, the inulin synthase of the present invention can be collected and purified as described in Example 1.

The process for producing inulin of the present invention comprises the step of allowing the inulin synthase of any one of the above (i) to (v), the culture fluid or cultured cells of a microorganism producing the enzyme, or the treated product thereof to contact with sucrose, thereby producing inulin (the process for producing inulin in (vi) above).

The phrase "allowing to contact with sucrose" means specifically, that the inulin synthase of any one of (i) to (v), the culture fluid or the cultured cells of a microorganism producing the enzyme, or the treated product thereof is added to a sugar solution containing sucrose, and then they are allowed to react under conditions wherein inulin is produced using sucrose as a substrate in the reaction solution. Thus, a reaction solution containing produced inulin can be obtained.

The above microorganism means the same as previously described in the explanation for the above inulin synthase of the present invention.

The term "culture fluid of a microorganism" that may be used for the process for producing inulin of the present invention includes the culture fluid itself (crude enzyme solution), or the product concentrated, immobilized or purified from the culture fluid, as described in detail above.

The term "cultured cells" that may be used for the process for producing inulin of the present invention includes intact viable cells, freeze-dried cells, or cells in the form of, for example, acetone powder, as described above.

Furthermore, as described above, the term "the treated product of cultured cells" that may be used for the process for producing inulin of the present invention includes, for example, disrupted products, cell extracts (liquid) and immobilized cells of the above cultured cells. The disrupted products of the cultured cells and the cell extracts (liquid) mean substances, extracts (liquid) and the like, which are obtained by disrupting the cells by a known disruption method, such as ultrasonic breaking, DynoMill disruption and French press disruption. Such substances and extracts (liquid) can also be used as a crude enzyme solution. In addition, "immobilized cells" means the above cells which are immobilized by a known immobilization method, such as an entrapment method or a carrier-binding method, and then subjected to cross-linking if necessary. Examples of the entrapment method include a method using natural polymers, such as carrageenan or alginic acid.

Appropriate sucrose concentration in the above sugar solution is, for example, 3 to 68% (w/w), and preferably, 10 to 60% (w/w). Other ingredients to be contained in the sugar solution are the same as those defined in the explanation for the above inulin synthase of the present invention.

The inulin synthase of the present invention, or the culture fluid or the cultured cells of a microorganism producing the enzyme, or the treated product thereof, which is used for reaction, should have a concentration at which sucrose (substrate) in the reaction solution can be efficiently used. For example, a preferred concentration is one that allows obtainment of a reaction solution in which the activity of inulin synthase is 0.4 to 20 unit/mL when 40 to 60% (w/w) sucrose is used.

Appropriate conditions that are preferably used for producing inulin using sucrose as a substrate consist of, for example, a reaction temperature of 20 to 70° C., and preferably 40 to 50° C., and a reaction solution with a pH range of 6 to 8. Further, a phosphate buffer can also be used for maintaining pH of the reaction solution. Reaction time may be appropriately changed depending on the amount of the inulin synthase of the present invention to be used herein. For example, the reaction time is 0.1 to 100 hours, and preferably, 0.5 to 72 hours.

Inulin produced in a reaction solution may be purified according to a known method.

For example, the obtained reaction solution is purified using ion exchange resin, activated carbon or the like, and then the product is concentrated under reduced pressure or using a reverse osmosis membrane, followed by cooling, thereby obtaining the crystal of inulin. Alternatively, an organic solvent, such as ethanol, is added to a reaction solution so as to be able to precipitate and collect inulin. However, examples of the method used herein are not limited to the above methods.

When reaction is performed at a temperature less than 40° C., the reaction product, inulin, which cannot be dissolved in the reaction solution may precipitate during reaction. In this case, crystal can be collected by a normal solid-liquid separation method.

Specifically, the process for producing inulin of the present invention can be implemented as described in Examples 2 and 3 in this specification.

Use of the process for producing inulin of the present invention enables obtainment of inulin products that are characterized by having an average degree of polymerization of 8 to 20, that is, they have a sharp distribution of molecular weight compared to the standard plant-derived inulin products (specifically, they all have the same quality).

By the use of the inulin synthase of the present invention, inulin of a uniform quality can be efficiently produced in large quantities using inexpensive sucrose as a raw material. It is easily deduced by a person skilled in the art that a combined use of a substance produced using inulin or fructan as a raw material with this enzyme enables direct production from sucrose.

Examples of a substance which is produced using inulin or fructone as a raw material include, but are not limited to, inulo-oligosaccharides, cyclic disaccharides of fructose (di-fructose anhydride), and cycloinulo-oligosaccharides (cyclofructan) and the like.

EXAMPLES

The present invention is more specifically described by the following Examples. However, these examples are not intended to limit the scope of the present invention.

Example 1

Function and Substrate Specificity of Inulin Synthase of the Present Invention

As a means to confirm that the inulin synthase of the present invention is a novel enzyme different from existing plant-derived enzymes, we examined whether inulin is produeced when the enzyme is allowed to act on kestose. In addition, to study the substrate specificity of the enzyme, we examined whether inulin is produced when the enzyme is allowed to act on a disaccharide other than sucrose, including lactose, trehalose, maltose and cellobiose.

(Preparation of Purified Enzyme Sample of Inulin Synthase of the Present Invention)

Bacillus sp. 217C-11 strain (FERM BP-7450) was shake-cultured in a liquid medium (pH 7 to 8) containing 0.5 to 2% (w/v) sucrose, 1% peptone, 0.5% yeast extract, 0.2% dipotassium phosphate and 0.05% magnesium sulfate at 30° C. for two days. Next, solid ammonium sulfate was added to the culture supernatant, and then a fraction precipitating at 70% saturation was collected using a centrifugal separator. Then, the precipitate was dissolved in 20 mM phosphate buffer of pH 7.0, put into a dialysis tube, and then dialyzed sufficiently with the same buffer, thereby obtaining a crude enzyme solution of the enzyme of the present invention. Subsequently, the crude enzyme solution was subjected to ion exchange chromatography and gel filtration chromatography using TSKgel DEAE TOYOPEARL 650 and TOYOPEARL HW55 manufactured by TOSOH CORPORATION, and Sephacryl S-300 manufactured by Pharmacia according to standard methods, thereby purifying the inulin synthase of the present invention. The thus purified inulin synthase was used in the next procedure as a purified enzyme sample.

(Analysis of Partial Amino Acid Sequence of Purified Enzyme Sample)

The N-terminal amino acid sequence of the above purified enzyme sample was determined according to the following procedure.

At first, the above purified enzyme sample was subjected to SDS-polyacrylamide gel electrophoresis (7.5%) accord ing to standard methods, transferred to a PVDF membrane, and then stained with Coomassie brilliant blue. A portion of the membrane corresponding to a target band of 50 kDa was then excised and washed with water sufficiently. The excised membrane was treated with 0.5% polyvinylpyrrolidone for 1 hour. Furthermore, the membrane was washed with water sufficiently, and then the N-terminal amino acid sequence was analyzed by HP G1005A Protein Sequencing System (Hewlett-Packard Company).

As a result, the N-terminal amino acid sequence of the above purified enzyme sample was determined to be Glu-Glu-Ile-Asn-Ser-Asp-Tyr-Thr-Ser-Ile-Trp-Ser-Arg-Gln-Gln-Ala-Glu-Lys-Val-Thr-Pro-Thr-Asp-Lys-Thr-Thr-Ala-Pro-Lys-Ile (SEQ ID NO: 1).

(Reaction for Producing Inulin)

100 mM solution of each of the above substrates was prepared. Then, an equivalent volume of the above purified enzyme sample was added (0.74μ/mL) to the solution, followed by reaction at 37° C. for 17 hours. The reaction products were analyzed by high performance liquid chromatography (HPLC).

The HPLC conditions were as follows.

HPLC Conditions
Column: ULTRON PS-80N (8×300 mm), SHINWA CHEMICAL INDUSTRIES, LTD.
Solvent: water
Flow rate: 0.5 mL/min
Temperature: 50° C.
Detector: Differential refractometer As a result, sucrose was the only substrate on which the enzyme of the present invention acted to produce inulin. The enzyme did not act at all on the disaccharides other than sucrose. When the enzyme acted on kestose, 90% or more of the enzyme remained intact and the main product was nystose, and no inulin was produced.

Example 2

Determination of Carbon Source Appropriate for Culturing Microorganisms

To examine which carbon source is preferable for culturing a microorganism when the inulin synthase of the present invention is collected from the microorganism, the following experiment was performed using Bacillus sp. 217C-11 strain (FERM BP-7450).

(Preparation of Crude Enzyme Solution)

Each of the 2% carbon sources shown in Table 1 below was added to a medium (pH 8) containing 1% peptone, 0.5% yeast extract, 0.3% malt extract, 0.2% potassium phosphate and 0.05% magnesium sulfate 7 hydrate, and then sterilized for preparation according to standard methods. Then, one platinum loop of Bacillus sp. 217C-11 strain (FERM BP-7450) was inoculated into each of these media. Shake culture was performed at 30° C. for 2 days, and then the activity of the inulin synthase of the present invention contained in the culture supernatant was measured.

(Measurement of Enzyme Activity)

0.2 mL of the above culture supernatant (enzyme solution) was added to 0.2 mL of a 20% sucrose solution dissolved in 40 mM phosphate buffer (pH 7). The mixture was allowed to react at 37° C. for 120 min, and then boiled for 5 min to stop reaction. Glucose produced by reaction was measured by a glucose oxidase method. This is because Bacillus sp. 217C-11 strain (FERM BP-7450) contains almost no invertase activity for degrading sucrose into glucose and fructose, and forms glucose as a by-product when it produces inulin by enzyme reaction using sucrose as a substrate. Here, the enzyme activity of 1 unit was considered to be the amount of enzyme which causes 1 μmole of glucose to produce in 1 min. Table 1 shows the results.

TABLE 1

Various carbon sources added to media and activity of the enzyme obtained therefrom

| Carbon source | Activity (u/mL) |
|---|---|
| sucrose | 0.62 |
| glucose | 0.08 |
| fructose | 0.05 |
| maltose | 0.03 |
| molasses | 1.73 |

As is clear from Table 1, high activity was obtained when Bacillus sp. 217C-11 strain (FERM BP-7450) was cultured using sucrose or a material containing the same (molasses) as a carbon source.

Example 3

Production of Inulin (1) Preparation of Crude Enzyme Solution

A medium (pH 8) containing 2% sucrose, 1% peptone, 0.5% yeast extract, 0.3% malt extract, 0.2% potassium phosphate and 0.05% magnesium sulfate-7 hydrate was sterilized for preparation according to standard methods. Then, one platinum loop of Bacillus sp. 217C-11 strain (FERM BP-7450) was inoculated into each of these media. Shake culture was performed at 30° C. for 2 days, and then a culture supernatant subjected to centrifugation for bacteria removal was obtained.

The activity of the enzyme contained in the culture supernatant was 0.8 u/mL when measured in a manner similar to Example 1 above.

Ammonium sulfate was added to the culture supernatant at 70% saturation. The resulting precipitate was dissolved in 20 mM phosphate buffer (pH 7), and then dialyzed against the buffer solution. The product was used as an enzyme solution in the following examples. The enzyme activity at this time was 16 u/mL.

(2) Reaction for Producing Inulin Using Crude Enzyme Solution 2 g of sucrose was dissolved in 2.75 mL of 44 mM phosphate buffer (pH 7), and then 0.25 mL of the enzyme solution obtained in (1) above was added to the solution to perform reaction at 37° C. Then, a part of the reaction solution was analyzed by HPLC under conditions similar to those employed in Example 1.

Figure 5:
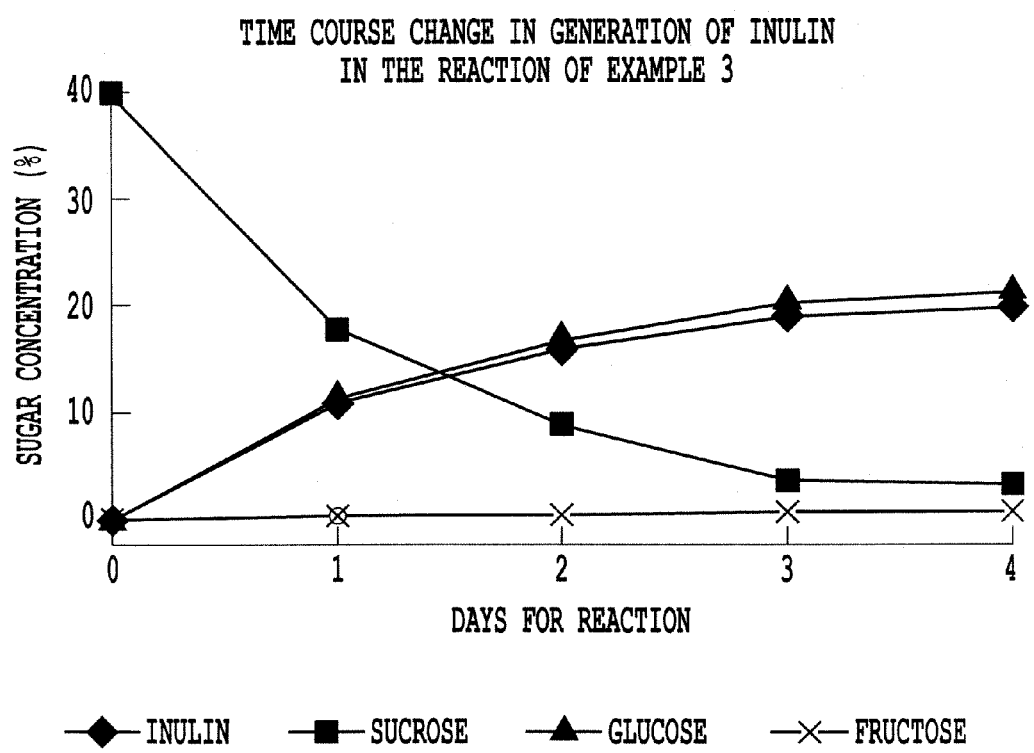
FIG. 5 shows the time-course change of inulin production in the reaction of Example 3.

FIG. 5 shows the results. As is clear from the figure, inulin was produced when the above enzyme solution was allowed to act on sucrose. Further, the reaction product increased with time and reached equilibrium within about 3 days. The yield from sucrose was about 50%.

(3) Identification of Reaction Product

A significant amount of inulin crystal separated from the reaction solution obtained in (2) above was collected by centrifugation (10,000 rpm, 15 min).

Subsequently, the solid content was dissolved in water at about 5%, 3-fold volume of ethanol was added to the solution for precipitation, and then the crystal was washed. The procedure was repeated twice. Finally, the obtained precipitate was freeze-dried and then weighed. The weight was 350 mg.

HPLC was performed for the sample in a manner similar to (2) above. The purity was 98.8%. Various identification/confirmation tests were performed for the obtained crystal, as follows.

(a) Nuclear Magnetic Resonance Absorption (NMR)

In addition to the crystal obtained above, the same analysis was performed for Levan derived from *Serratia Levanicum* (Wako Pure Chemical Industries, Ltd.) having β-(2→6) linkages as a reference example using a commercially available inulin (Product name RAFTILINE HP, manufactured by ORAFTI) as a standard. A spectrometer used as an NMR apparatus herein was JEOL lambda-500 FT-NMR spectrometer 500 MHz and measurement was performed in deuterium oxide.

Figure 6A:
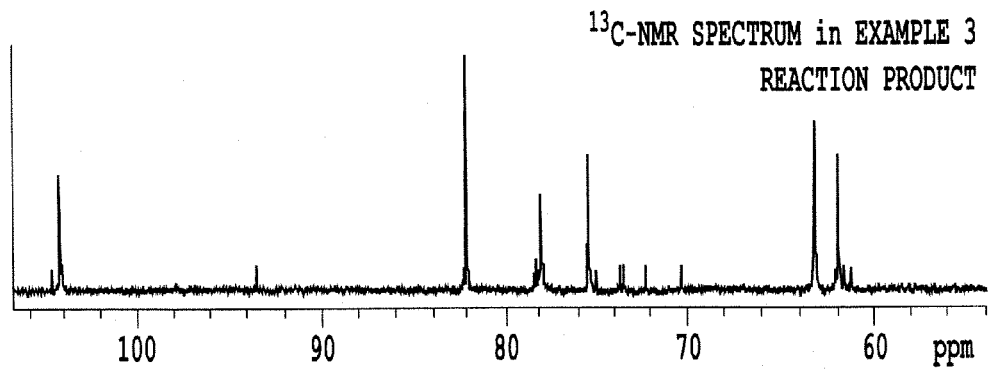
FIG. 6 shows $^{13}$C-NMR spectrum for each substance in Example 3. "a", "b" and "c" represent $^{13}$C-NMR spectrum for reaction products, commercially available inulin and a reagent, Levan (Wako Pure Chemical Industries, Ltd.), respectively.
Figure 6B:
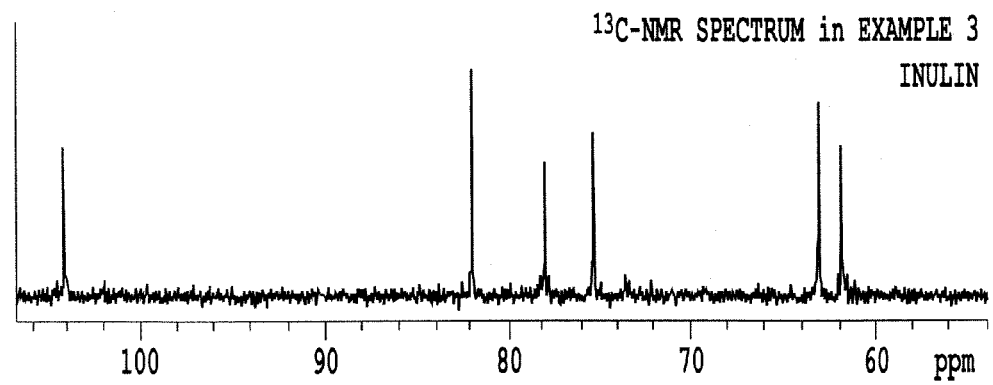
Figure 6C:
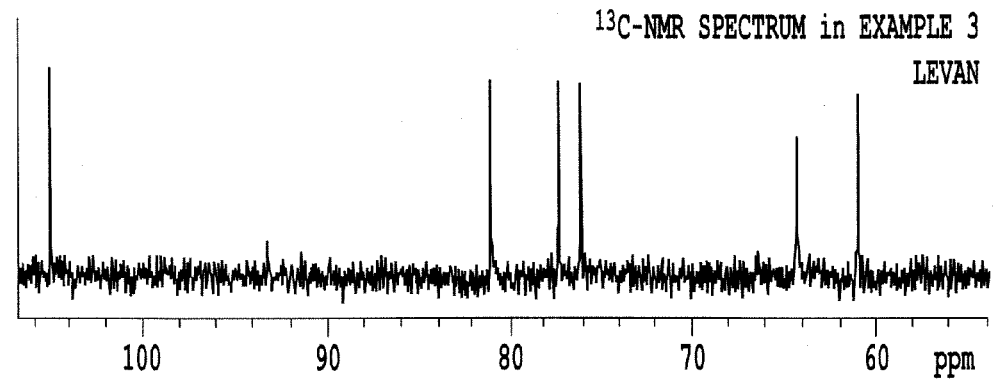
Figure 7A:
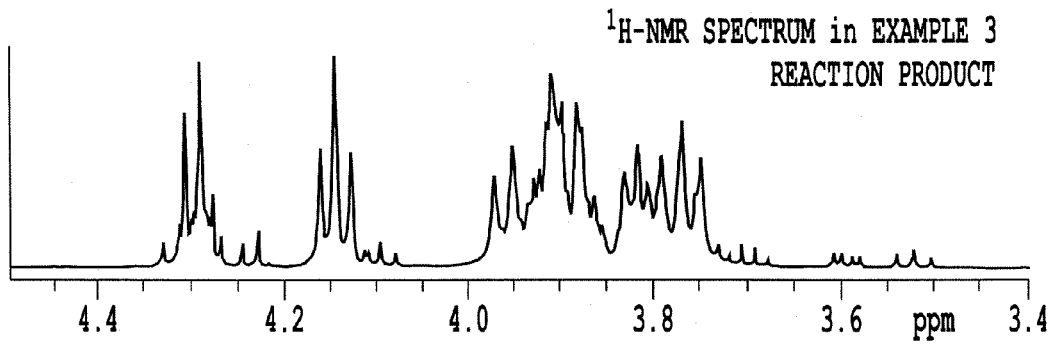
FIG. 7 shows $^1$H-NMR spectrum for each substance in Example 3. "a", "b" and "c" represent $^1$H-NMR spectrum for reaction products, commercially available inulin, and a reagent, Levan (Wako Pure Chemical Industries, Ltd.), respectively.
Figure 7B:
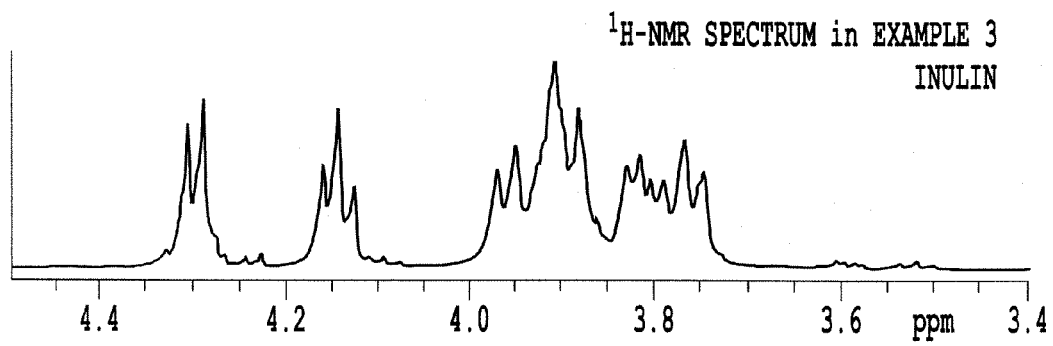
Figure 7C:
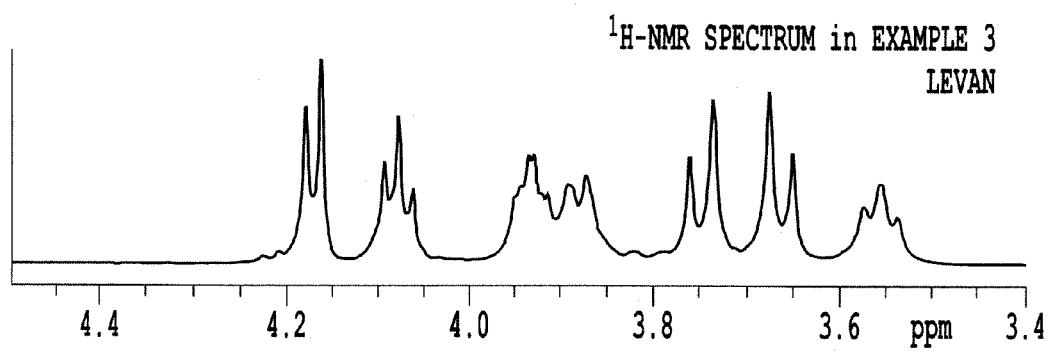

FIG. 6 shows all $^{13}$C-NMR spectra obtained for each substance, and FIG. 7 shows all $^1$H-NMR spectra. As a result of comparison with these, it was found that the above crystal showed a peak pattern identical to that of inulin.

(b) Estimation of Molecular Weight by HPLC

The above crystal was subjected to high performance liquid chromatography (HPLC) under the conditions shown below, and then the molecular weight was estimated. In addition, RAFTILINE HP (average degree of polymerization: 23) and RAFTILINE ST (average degree of polymerization: 10), both manufactured by ORAFTI, were used as standard samples. An analytical curve was prepared and calculated. The retention time of RAFTILINE HP was 17.23 min, the retention time of RAFTILINE ST was 17.75 min, and the retention time of the above crystalline substance was 17.39 min. It was estimated that the average degree of polymerization of the above crystalline substance was 18.

HPLC Conditions

Column: TOSOH TSK-GEL G3000PWXL (7.8×300 mm)
Solvent: water
Flow rate: 0.5 mL/min
Temperature: 50° C.
Detector: differential refractometer (c) Digestion Test with Inulinase The reaction solution obtained after commercially available inulinase (Product name: Fructozyme L, manufactured by NOVO) was allowed to act on the above crystal was analyzed by HPLC under conditions similar to Example 1. As a result, the above crystal was completely degraded into glucose and fructose, and the production ratio was 1:17. The average degree of polymerization of the crystal was estimated to be 18.

(d) Mass Spectrum

When the molecular weight of the above crystal was measured by mass spectrum, the average degree of polymerization of the crystal ranged from 17 to 18.

Based on the above results (a) to (d), it was determined that the crystal obtained using sucrose as a raw material was inulin.

Example 4

(1) Preparation of Crude Enzyme

Culturing was performed under the same conditions as those of Example 3 (1), and a crude enzyme solution with enzyme activity of 0.6 u/mL was prepared.

(2) Reaction for Producing Inulin Using Crude Enzyme 80 g of sucrose was added to and dissolved in 20 mL of 200 mM phosphate buffer (pH 7) and 100 mL of a crude enzyme solution. Reaction was performed at 37° C. for 4 days while stirring at 147 rpm.

Next, the reaction solution was analyzed by HPLC under conditions similar to Example 1. The reaction product increased with time and reached equilibrium within 3 or 4 days. In addition, the yield from sucrose was about 37.5%.

(3) Identification of Reaction Product

The reaction solution obtained in (2) above was concentrated about 2-fold using a reverse osmosis membrane, and then cooled at 4° C. so as to separate out inulin crystal. Solid-liquid separation was performed by centrifugation (10,000 rpm, 15 min) to collect a precipitated portion, which was then freeze-dried and weighed in a manner similar to Example 2 (2). The weight was 5 g. The purity of this sample as analyzed by HPLC (under conditions similar to Example 1) was 99.6%. Various identification/confirmation tests were performed for the obtained crystal in a manner similar to Example 3 (3), as follows.

(a) Nuclear magnetic resonance absorption (NMR)

The above crystal showed a peak pattern identical to that of inulin. A spectrometer used as an NMR apparatus was JEOL lambda-500 FT-NMR spectrometer 500 MHz and measurement was performed in deuterium oxide.

(b) Estimation of Molecular Weight by HPLC

The molecular weight of the above crystal was estimated by analyzing several times under the HPLC conditions shown in Example 3 (3). As a result, the retention time of RAFTILINE HP was 17.23 min, the retention time of RAFTILINE ST was 17.75 min, and the retention times of the above crystalline substance were 17.59 min, 17.70 min, 17.78 min and 17.82 min. It was estimated that the average degree of polymerization of the crystalline substance ranged from 8 to 14.

(c) Mass Spectrum

When the molecular weight of the above crystal was measured by mass spectrum, the average degree of polymerization of the above crystal ranged from 13 to 14.

Based on the above results (a), (b) and (c), it was determined that the substance obtained using sucrose as a raw material was inulin.

All publications, patents and patent applications cited herein are incorporated herein by reference in their entirety.

INDUSTRIAL APPLICABILITY

The present invention provides a novel inulin synthase for producing inulin of uniform quality with high purity in large quantities by an efficient and industrially practical method, and a process for producing inulin using the novel inulin synthase.

The invention claimed is:

1. An inulin synthase having the following function and substrate specificity: being capable of acting on sucrose to produce inulin having an average degree of polymerization of 17 to 20, but not acting on ketose, maltose, lactose, trehalose and cellobiose and which is isolated from *Bacillus* sp. 217C-11 strain (FERM BP-7450).

2. The inulin synthase of claim 1, wherein an N-terminal amino acid sequence of the inulin synthase comprises SEQ ID NO: 1.

3. A process for producing inulin, which comprises contacting an inulin synthase, a culture fluid of a microorganism producing said inulin syntase, cultured cells of a microorganism producing said inulin synthase, disrupted products of said cultured cells, cell extracts of said cultured cells, immobilized cells of said cultured cells, or a combination of these with sucrose to produce inulin, wherein the inulin synthase has the following function and substrate specificity: being capable of acting on sucrose to produce inulin having an average degree of polymerization of 17 to 20, but not acting on ketose, maltose, lactose, trehalose and cellobiose and wherein the inulin synthase is encoded by a nucleotide sequence from *Bacillus* sp. 217C-11 strain (FERM BP-7450).

4. The process for producing inulin of claim 3, wherein-an N-terminal amino acid sequence of said inulin synthase comprises SEQ ID NO:1.

\* \* \* \* \*